United States Patent
Horsey et al.

(10) Patent No.: US 6,472,456 B1
(45) Date of Patent: Oct. 29, 2002

(54) FLAME RETARDANT COMPOSITIONS

(75) Inventors: Douglas Wayne Horsey, Briarcliff Manor, NY (US); Stephen Mark Andrews, New Fairfield, CT (US); Leonard Harris Davis, New City, NY (US); Darrell David Dyas, Jr., Acworth, GA (US); Robert Leo Gray, West Lafayette, IN (US); Anunay Gupta, Edison, NJ (US); Bruce Vincent Hein, Marietta, GA (US); Joseph Stephen Puglisi, Crompond; Ramanathan Ravichandran, Nanuet, both of NY (US); Paul Shields, Rivervale, NJ (US); Rangarajan Srinivasan, Tarrytown, NY (US)

(73) Assignee: Ciba Specialty Chemicals Corp., Tarrytown, NY (US)

( * ) Notice: Subject to any disclaimer, the term of this patent is extended or adjusted under 35 U.S.C. 154(b) by 0 days.

(21) Appl. No.: 09/502,239

(22) Filed: Nov. 3, 1999

Related U.S. Application Data

(63) Continuation-in-part of application No. 09/104,718, filed on Jun. 25, 1998, now abandoned
(60) Provisional application No. 60/051,331, filed on Jun. 30, 1997.

(51) Int. Cl.[7] .................... C08K 5/3415; C08K 5/3417; C08K 3/32; C08K 5/49; C08K 5/3467
(52) U.S. Cl. .................... 524/99; 524/141; 524/145; 524/415; 524/91
(58) Field of Search .................. 524/371, 100, 524/101, 102, 103, 104, 415, 141, 145, 91, 99

(56) References Cited

U.S. PATENT DOCUMENTS

| | | | |
|---|---|---|---|
| 4,173,561 A | 11/1979 | Tabana et al. ........... 260/45.75 |
| 4,978,669 A | 12/1990 | Kazmierczak et al. ......... 529/99 |
| 5,004,770 A | 4/1991 | Cortolano et al. ............ 524/99 |
| 5,021,486 A | 6/1991 | Galbo ........................ 524/100 |
| 5,025,050 A | 6/1991 | Torres .......................... 524/91 |
| 5,077,340 A | 12/1991 | Ravichandran et al. ..... 525/203 |
| 5,096,950 A | 3/1992 | Galbo et al. ................... 524/99 |
| 5,112,890 A | 5/1992 | Behrens et al. ............... 524/95 |
| 5,118,736 A | 6/1992 | Ravichandran et al. ..... 524/100 |
| 5,145,893 A | 9/1992 | Galbo et al. ................... 546/19 |
| 5,204,473 A | 4/1993 | Winter et al. ............... 546/188 |
| 5,280,056 A * | 1/1994 | Lardry et al. |
| 5,300,544 A | 4/1994 | Galbo et al. |
| 5,359,069 A | 10/1994 | Galbo et al. ................... 546/19 |
| 5,393,812 A * | 2/1995 | Haley et al. |
| 5,810,914 A * | 9/1998 | Okisaka et al. |
| 5,844,026 A | 12/1998 | Galbo et al. ................. 524/100 |
| 5,859,147 A * | 1/1999 | Torre et al. |
| 5,980,783 A * | 11/1999 | Gugumus |
| 6,117,995 A * | 9/2000 | Zedda et al. |

FOREIGN PATENT DOCUMENTS

| | | |
|---|---|---|
| EP | 0366057 | 5/1990 |
| EP | 0792911 | 9/1997 |
| WO | 90/06691 | 6/1990 |

* cited by examiner

Primary Examiner—Peter Szekely

(57) ABSTRACT

Polyolefins, especially polypropylene, can be made flame retardant by the incorporation therein of a synergistic mixture of a selected hindered amine substituted by an alkoxy, cydoalkoxy or hydroxyalkoxy moiety and a selected organic or inorganic brominated and/or phosphorus containing flame retardant, such as ammonium polyphosphate or decabromodiphenyl oxide wherein the amount of organic or inorganic flame retardant required to achieve an acceptable level of flame retardancy is significantly reduced compared to that needed when the hindered amine is not present.

12 Claims, No Drawings

FLAME RETARDANT COMPOSITIONS

This application claims the benefit under 35 USC 119(e) of U.S. Provisional Application Serial No. 60/051,331, filed on Jun. 30, 1997; and is a continuation-in-part of application Serial No. 09/104,718, filed on Jun. 25, 1998, now abandoned.

The instant invention pertains to a method of flame retarding a polymeric substrate by adding thereto an effective flame retarding amount of a synergistic mixture of a selected hindered amine compound and an organic or inorganic flame retardant which contains bromine and/or phosphorus moieties.

BACKGROUND OF THE INVENTION

The hindered amines have long been recognized as light and/or as thermal stabilizers for a host of organic materials subject to degradation induced by oxygen, heat or actinic light. The patent and academic publication literature is replete with references to these hindered amine compounds and their valuable stabilizing efficacies. There is no mention or suggestion in any of such references that the hindered amines themselves are also flame retardants per se.

Particularly relevant are U.S. Pat. Nos. 5,004,770; 5,096,950; 5,204,473; 5,300,544; 5,844,026; 6,117,995 and 6,271,377. These references pertain to various N-hydrocarbyloxy substituted hindered amines (so called NOR and NOROL hindered amines) and to various compositions stabilized therewith. As mentioned above, none of these reference disclose or even hint that the compositions stabilized with the NOR or NOROL hindered amines alone are flame retardant. This inherent property was never discovered, not even serendipitously, until the present invention was made. That this is so, is in itself evidence that even those of considerable skill in the hindered amine stabilizer art were quite surprised by this unexpected discovery. The fact that a large amount of an inorganic or organic classical bromine and/or phosphorus containing flame retardant could be substituted by a small amount of a NOR or NOROL hindered amine and still achieve very acceptable flame retardancy was also quite unexpected. This is highly beneficial for the environment and for safety reasons. Accordingly, polymeric substrate compositions made flame retardant by incorporating therein a synergistic mixture of a NOR or NOROL hindered amine plus a classic inorganic or organic bromine and/or phosphorus containing flame retardant is also quite surprising, unexpected and clearly not obvious to those of skill in this stabilizer art. This invention affords the public a valuable method for flame retarding polymers which cannot be gleaned from any of the prior art references.

U.S. Pat. No. 5,393,812 does describe polyolefin compositions which are made flame retardant by a combination of a halogenated hydrocarbyl phosphate or phosphonate ester flame retardant in combination with a alkoxyamine functional hindered amine, but there is no suggestion that the hindered amine itself is responsible for the flame retardancy, but rather that the hindered amine is preventing delustering and other undesirable effects from occurring in these polyolefin compositions.

European Application No. 0 792 911 A2, published after the filing date of the parent provisional application Serial No. 60/051,331, discloses that alkoxyamine functional hindered amines may have some flame retarding properties, but are quite effective when used to enhance the flame retarding efficacy of tris(trihalogenopentyl) phosphate flame retardants. This publication is somewhat ambivalent as to whether the alkoxyamine functional hindered amine are really themselves flame retardants in the absence of the recognized phosphate flame retardant.

The flame retardant (FR) market today is comprised of products which function to interfere with the combustion process by chemical and/or physical means. Mechanistically these FRs have been proposed to function during combustion of an article in either the gas phase, the condensed phase or both. The organohalogens are proposed to generate halogen species (e.g. HX) which interferes in the gas phase with free radical organic "fuel" from the polymer substrate. Synergists are proposed to react with HX to form additional chemical species with interfere with combustion in the gas phase, such as reaction of antimony oxide with HX to form antimony halide and water vapor. Still other flame retardant classes are proposed to impart efficacy in the "condensed" phase such as forming a protective char layer on the polyester, or forming an intumescent or foaming on the polymer surface. The char or intumescent layer is thought either to prevent organic fuel from migrating from the polymer into the vapor phase where it can fuel combustion, or the char can act as a thermal shield to protect the underlying polymer article from thermally induced decomposition and generation of fuel. Phosphorus compound of various classes (e.g. halo- or non-halogenated) are an example. Further still, other classes of compounds are proposed to function in the condensed and/or vapor phase. Metal hydrates or metal oxides are proposed to generate water vapor under thermal conditions, the water acting to dilute the fuel mix in the combustion zone and to remove heat from the flame zone via conversion of water to vapor. Alumina trihydrate, magnesium hydroxide or oxide, and other compounds are reported to function in this way.

These state of the art chemistries described above have various detrimental aspects in addition to the effective flame retarding attributes mentioned. Certain organobrominated compounds are under governmental scrutiny for the generation of toxic by-products during the production or combustion such as dioxanes from polybrominated diphenyl oxides. Certain metal-containing flame retardants, notably antimony oxides, are under scrutiny for worker exposure and toxicity reasons. Antimony oxides often contain trace amounts of arsenic compounds which are suspected cancinogens. Overall, a growing concern has arisen regarding the generation of smoke and toxic gases which are evolved from these flame retardants during a fire. While the classic FRs may be effective combustion suppressants, the toxic gases they form pose a threat to human exposure.

The instant invention alleviates some of the detrimental aspects of the current state of the art which the use of large amounts of commercial flame retardants pose. The instant NOR or NOROL hindered amines are non-halogenated and free of heavy metals, thus avoiding generation of corrosive HX gases and avoiding exposure to toxic metals. In some applications, the instant invention provides a direct replacement for current FR systems where the instant NOR or NOROL hindered amine compounds provide a complimentary enhancment or synergistic system for heavy metals (e.g. antimony oxide replacement in ABS) where good flame retardancy can be achieved by using less classic FR agent in the presence of the instant NOR or NOROL hindered amine compound.

DETAILED DISCLOSURE

The instant invention pertains to a flame retardant composition which comprises (a) a polymer substrate, preferably a polyolefin, most preferably polypropylene, and
(b) an effective flame retarding amount of a synergistic mixture of
(i) a hindered amine of formula A:

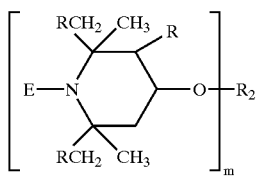

(A)

wherein
E is alkoxy of 1 to 18 carbon atoms, cycloalkoxy of 5 to 12 carbon atoms or aralkoxy of 7 to 15 carbon atoms, or E is —O—T—(OH)$_b$, preferably E is methyoxy, propoxy, cydohexyloxy or octyloxy, most preferably cyclohexyloxy,
T is a straight or branched chain alkylene of 1 to 18 carbon atoms, cycloalkylene of 5 to 18 carbon atoms, cycloalkenylene of 5 to 18 carbon atoms, a straight or branched chain alkylene of 1 to 4 carbon atoms substituted by phenyl or by phenyl substituted by one or two alkyl groups of 1 to 4 carbon atoms;
b is 1, 2 or 3 with the proviso that b cannot exceed the number of carbon atoms in T, and when b is 2 or 3, each hydroxyl group is attached to a different carbon atoms of T;
R is hydrogen or methyl,
m is 1 to 4,
when m is 1,
R$_2$ is hydrogen, C$_1$–C$_{18}$alkyl or said alkyl optionally interrupted by one or more oxygen atoms, C$_2$–C$_{12}$alkenyl, C$_6$–C$_{18}$aryl, C$_7$–C$_{18}$aralkyl, glycidyl, a monovalent acyl radical of an aliphatic, cycloaliphatic or aromatic carboxylic acid, or a carbamic acid, preferably an acyl radical of an aliphatic carboxylic acid having 2–18 C atoms, of a cycloaliphatic carboxylic acid having 5–12 C atoms or of an aromatic carboxylic acid having 7–15 C atoms or:

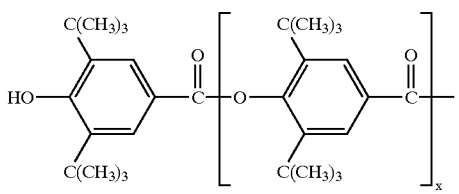

wherein x is 0 or 1;

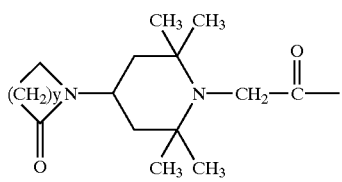

wherein y is 2–4;
when m is 2,
R$_2$ is C$_1$–C$_{12}$alkylene, C$_4$–C$_{12}$alkenylene, xylylene, a divalent acyl radical of an aliphatic, cytioaliphatic, aralphatic or aromatic dicarboxylic acid or of a dicarbamic acid, preferably an acyl radical of an aliphatic dicarboxylic acid having 2–18 C atoms, of a cycloaliphatic or aromatic dicarboxylic acid having 8–14 C atoms, or of an aliphatic, cydoaliphatic or aromatic dicarbamic acid having 8–14 C atoms:

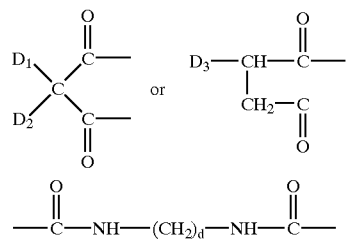

wherein D$_1$ and D$_2$ are independently hydrogen, an alkyl radical containing up to 8 carbon atoms, an aryl or aralkyl radical including 3,5-di-t-butyl-4hydroxybenzyl radical, D$_3$ is hydrogen, or an alkyl or alkenyl radical containing up to 18 carbon atoms, and d is 0–20;
when m is 3, R$_2$ is a trivalent acyl radical of an aliphatic, unsaturated aliphatic, cycloaliphatic, or aromatic tricarboxylic acid;
when m is 4, R$_2$ is a tetravalent acyl radical of a saturated or unsaturated aliphatic or aromatic tetracarboxylic acid including 1,2,3,4-butanetetracarboxylic acid, 1,2,3,4-but-2-ene-tetracarboxylic, and 1,2,3,5- and 1,2,4, 5pentanetetracarboxylic acid; or
wherein the hindered amine compound is a mixture of N,N',N'''-tris{2,4-bis[(1-hydrocarbyloxy-2,2,6,6-tetramethylpiperidin-4-yl)alkylamino]-s-triazin-6-yl}-3,3'-ethylenediiminodipropylamine; N, N', N'''-tris{2,4-bis[(1-hydrocarbyloxy-2,2,6,6-tetramethylpiperidin-4-yl) alkyl-amino]-s-triazin-6-yl}-3,3'-ethylenediiminodipropylamine, and bridged derivatives as described by formulas I, II, IIA and III:

R$_1$NH—CH$_2$CH$_2$CH$_2$NR$_2$CH$_2$CH$_2$NR$_3$CH$_2$CH$_2$CH$_2$NHR$_4$ (I)

T-E$_1$-T$_1$ (II)

T-E$_1$ (IIA)

G-E$_1$-G$_1$-E$_1$-G$_2$ (III)

where in the tetraamine of formula I:

R$_1$ and R$_2$ are the s-triazine moiety E$_2$; and one of R$_3$ and R$_4$ is the s-triazine moiety E$_2$ with the other of R$_3$ or R$_4$ being hydrogen, $E_2$ is:

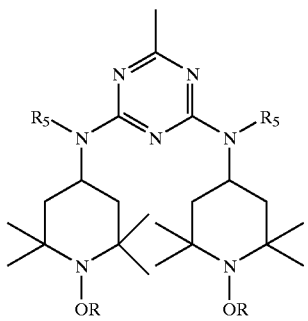

R is methyl, propyl, cyclohexyl or octyl, preferably cyclohexyl, $R_5$ is alkyl of 1 to 12 carbon atoms, preferably n-butyl, where in the compound of formula II or IIA when R is propyl, cyclohexyl or octyl, T and $T_1$ are each a substituted by $R_1$–$R_4$ as is defined for formula I, where (1) one of the s-triazine moieties $E_2$ in each tetraamine is replaced by the group $E_1$ which forms a bridge between two tetraamines T and $T_1$, $E_1$ is:

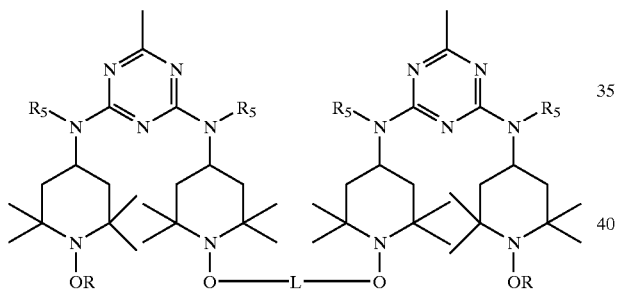

or (2) the group $E_1$ can have both termini in the same tetraamine T as in formula IIA where two of the $E_2$ moieties of the tetraamine are replaced by one $E_1$ group, or (3) all three s-triazine substituents of tetraamine T can be $E_1$ such that one $E_1$ links T and $T_1$ and a second $E_1$ has both termini in tetraamine T, L is propanediyl, cyclohexanediyl or octanediyl;

where in the compound of formula III:

G, $G_1$ and $G_2$ are each tetraamines substituted by $R_1$–$R_4$ as defined for formula I, except that G and $G_2$ each have one of the s-triazine moieties $E_2$ replaced by $E_1$, and $G_1$ has two of the triazine moieties $E_2$ replaced by $E_1$, so that there is a bridge between G and $G_1$ and a second bridge between $G_1$ and $G_2$;

which mixture is prepared by reacting two to four equivalents of 2,4-bis[(1-hydrocarbyl-oxy-2,2,6,6-piperidin-4-yl)butylamino]-6-chloro-s-triazine with one equivalent of N,N'-bis(3-aminopropyl)ethylenediamine;

or the hindered amine is a compound of the formula IIIb:

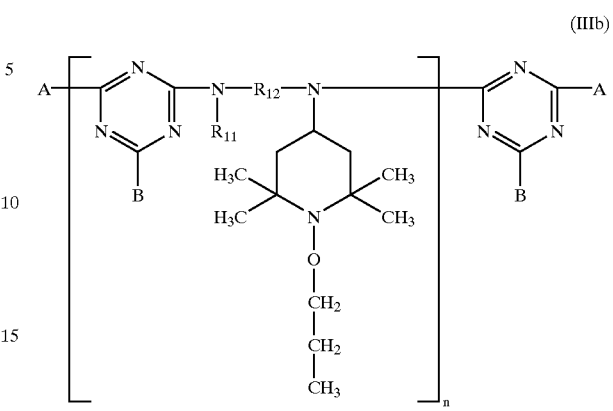

in which the index n ranges from 1 to 15;

$R_{12}$ is $C_2$–$C_{12}$alkylene, $C_4$–$C_{12}$alkenylene, $C_5$–$C_7$cycloalkylene, $C_5$–$C_7$ cycloalkylene-di($C_1$–$C_4$alkylene), $C_1$–$C_4$alkylenedi($C_5$–$C_7$cycoalkylene), phenylenedi($C_1$–$C_4$alkylene) or $C_4$–$C_{12}$alkylene interrupted by 1,4piperazinediyl, —O— or >N—$X_1$ with $X_1$ being $C_1$–$C_{12}$acyl or ($C_1$–$C_{12}$alkoxy)carbonyl or having one of the definitions of $R_{14}$ given below except hydrogen; or $R_{12}$ is a group of the formula (Ib') or (Ic'):

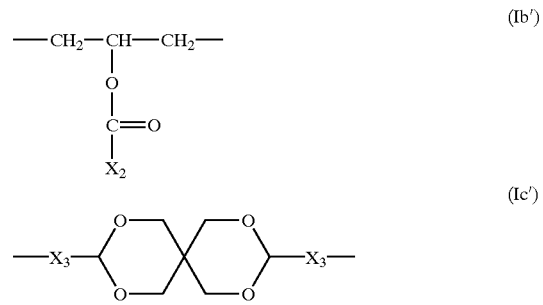

with m being 2 or 3, $X_2$ being $C_1$–$C_{18}$alkyl, $C_5$–$C_{12}$cycloalkyl which is unsubstituted or substituted by 1, 2 or 3 $C_1$–$C_4$alkyl, phenyl which is unsubstituted or substituted by 1, 2 or 3 $C_1$–$C_4$alkyl or $C_1$–$C_4$alkoxy; $C_7$–$C_9$phenylalkyl which is unsubstituted or substituted on the phenyl by 1, 2 or 3 $C_1$–$C_4$alkyl; and the radicals $X_3$ being independently of one another $C_2$–$C_{12}$alkylene;

$R_{13}$ $R_{14}$ and $R_{15}$, which are identical or different, are hydrogen, $C_1$–$C_{18}$alkyl, $C_5$–$C_{12}$cycloalky which is unsubstituted or substituted by 1, 2 or 3 $C_1$–$C_4$alkyl; $C_3$–$C_{18}$alkenyl, phenyl which is unsubstituted or substituted by 1, 2 or 3 $C_1$–$C_4$alkyl or $C_1$–$C_4$alkoxy; $C_7$–$C_9$phenylalkyl which is unsubstituted or substituted on the phenyl by 1, 2 or 3 $C_1$–$C_4$alkyl; tetrahydrofurfuryl or $C_2$–$C_4$alkyl which is substituted in the 2, 3 or 4 position by —OH, $C_1$–$C_8$alkoxy, di($C_1$–$C_4$alkyl) amino or a group of the formula (Ie'):

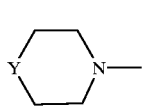
(Ie')

with Y being —O—, —CH$_2$—, —CH$_2$CH$_2$— or >N—CH$_3$, or —N(R$_{14}$)(R$_{15}$) is additionally a group of the formula (Ie'); the radicals A are independently of one another —OR$_{13}$,—N(R$_{14}$)(R$_{15}$) or a group of the formula (IIId):

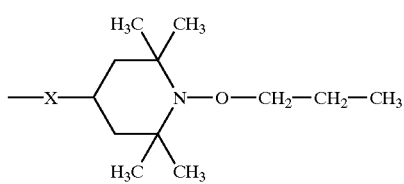
(IIId)

X is —O— or >N—R$_{16,}$

R$_{16}$ hydrogen, C$_1$–C$_{18}$alkyl, C$_3$–C$_{18}$alkenyl, C$_5$–C$_{12}$cycloalkyl which is unsubstituted or substituted by 1, 2 or 3 C$_1$–C$_4$alkyl; C$_7$–C$_9$phenylalkyl which is unsubstituted or substituted on the phenyl by 1, 2 or 3 C$_1$–C$_4$alkyl; tetrahydrofurfuryl, a group of the formula (IIIf):

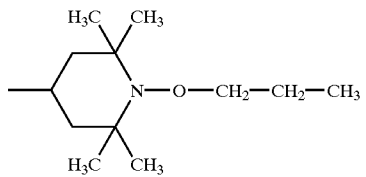
(IIIf)

or C$_2$–C$_4$alkyl which is substituted in the 2, 3 or 4 position by —OH, C$_1$–C$_8$alkoxy, di(C$_1$–C$_4$alkyl)amino or a group of the formula (Ie');

R$_{11}$ has one of the definitions given for R$_{16}$; and the radicals B have independently of one another one of the definitions given for A;

(ii) a brominated and/or a phosphorus containing flame retardant with the proviso that when the polymeric substrate is polypropylene, the flame retardant is not a halogenated hydrocarbyl phosphate or phosphonate.

Preferably the hindered amine compounds are the mixture of compounds of formula I, II, IIA and III where R is cyclohexyl; bis(1-octyloxy-2,2,6,6tetramethylpiperidin-4-yl) sebacate; 1-(2-hydroxy-2-methylpropoxy)-4-octadecanoyloxy-2,2,6,6-tetramethylpiperidine, or the compound of formula:

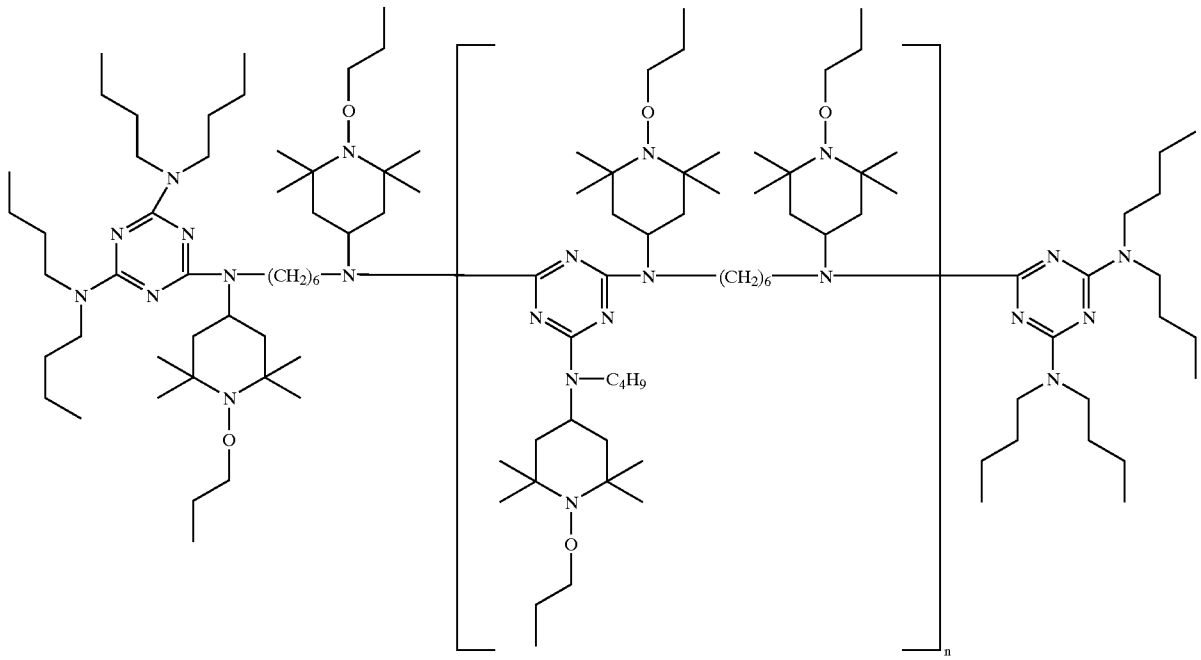

In the structures A to R, if any substituents are $C_1$–$C_{18}$ alkyl, they are for example methyl, ethyl, n-propyl, n-butyl, sec-butyl, tert-butyl, n-hexyl, n-octyl, 2-ethylhexyl, n-nonyl, n-decyl, n-undecyl, n-dodecyl, n-tridecyl, n-tetradecyl, n-hexadecyl or n-octadecyl. Typical cycloalkyl groups include cyclopentyl and cydohexyl; typical cycloalkenyl groups include cyclohexenyl; while typical aralkyl groups include benzyl, alpha-methyl-benzyl, alpha, alpha-dimethylbenzyl or phenethyl. $C_1$–$C_{12}$ alkyl and cyclohexyl are preferred.

If $R_2$ is a monovalent acyl radical of a carboxylic acid, it is for example an acyl radical of acetic acid, stearic acid, salicydic acid, benzoic acid or β-(3,5-di-tert-butyl-4-hydroxyphenyl) propionic acid.

If $R_2$ is a divalent acyl radical of a dicarboxylic acid, it is for example an acyl radical of oxalic acid, adipic acid, succinic acid, suberic acid, sebacic acid, phthalic acid dibutylmalonic acid, dibenzylmalonic acid or butyl-(3,5-di-tert-butyl-4-hydropxybenzyl)-malonic acid, or bicydoheptenedicarboxylic acid, with succinates, sebacates, phthalates and isophthalates being preferred.

If $R_2$ is a divalent acyl radical of a dicarbamic acid, it is for example an acyl radical of hexamethylenedicarbamic acid or of 2,4-toluylenedicarbamic acid.

The instant NOR hindered amine compounds as described above are known in the prior art and are prepared as taught in U.S. Pat. Nos. 5,004,770; 5,096,950; 5,204,473; 5,300,544; 5,844026; 6,117,995; and 6,271,377.

Preferably, the polymer substrate is selected from the group of resins consisting of the polyolefins, the thermoplastic olefins, styrenic polymers and copolymers, and ABS.

(b) 1-cydohexyloxy-2,2,6,6-tetramethyl-4-octadecylaminopiperidine;

(c) bis(1-octyloxy-2,2,6,6-tetramethylpiperidin-4-yl) sebacate;

(d) 2,4-bis[(1-cydohexyloxy-2,2,6,6-tetramethylpipeddin-4-yl)butylamino]-6-(2-hydroxy-ethylamino-s-triazine;

(e) bis(1-cydohexyloxy-2,2,6,6tetramethylpiperidin-4yl) adipate;

(f) the oligomeric compound which is the condensation product of 4,4'-hexamethylene-bis(amino-2,2,6,6-tetramethylpiperidine) and 2,4-dichloro-6-[(1-octyloxy-2,2,6,6-tetramethyl-piperidin-4-yl) butylamino]-s-triazine end-capped with 2-chloro4,6-bis(dibutylamino)-s-triazine;

(g) the oligomeric compound which is the condensation product of 4,4'-hexamethylene-bis(amino-2,2,6,6-tetramethylpiperidine) and 2,4-dichloro-6-[(1-cyclohexyloxy-2,2,6-tetra-methylpiperidin-4-yl) butylamino]-s-triazine end-capped with 2-chloro-4,6-bis(dibutylamino)-s-triazine;

(h) 2,4bis[(1-cydohexyloxy-2,2,6,6-piperidin-4-yl) butylamino]-6-chloro-s-triazine;

(i) 1-(2-hydroxy-2-methylpropoxy)-4-octadecanoyloxy-2,2,6,6-tetramethylpiperidine; or (j) the compound of formula:

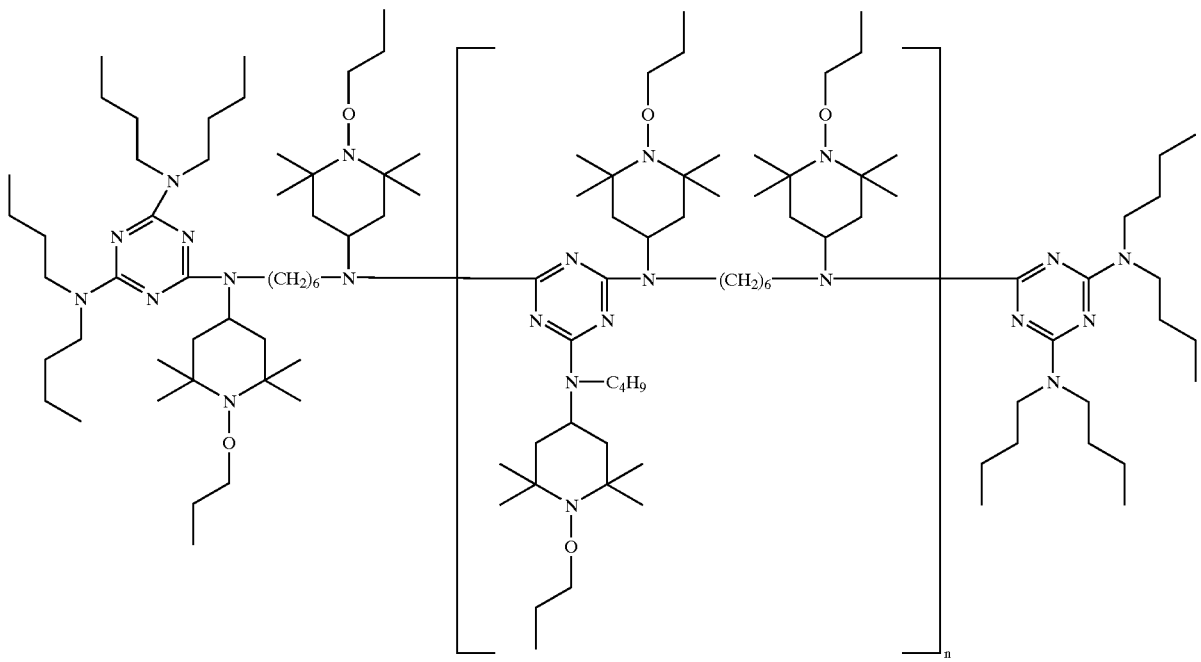

More preferably, the polymer substrate is polypropylene, polyethylene, thermoplastic olefin (TPO), ABS and high impact polystyrene.

Most preferably, polymer substrate is polypropylene, polyethylene or thermoplastic olefin (TPO).

Preferably, the NOR or NOROL hindered amine of component (i) is (a) the mixture of compounds of formula I, II, IIA and III where R is cyclohexyl;

Most preferably, the compound of component (i) is:

(a) the mixture of compounds of formula I, II, IIA and III where R is cyclohexyl;

(c) bis(1-octyloxy-2,2,6,6-tetramethylpiperidin-4-yl) sebacate;

(i) 1-(2-hydroxy-2-methylpropoxy)-4-octadecanoyloxy-2,2,6,6-tetramethylpiperidine; or (j) the compound of formula:

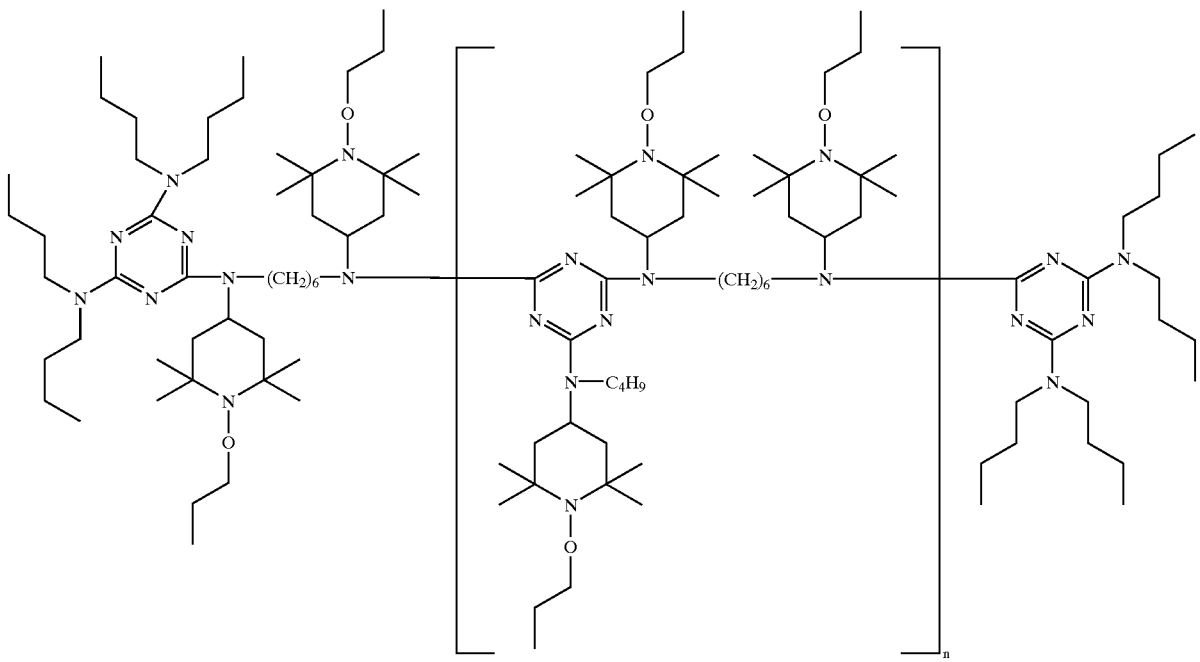

The effective flame retarding amount of the hindered amine is that needed to show flame retarding efficacy as measured by one of the standard methods used to assess flame retardancy. These include the NFPA 701 Standard Methods of Fire Tests for Flame-Resistant Textiles and Films, 1989 and 1996 editions; the UL 94 Test for Flammability of Plastic Materials for Parts in Devices and Appliances, 5th Edition, Oct. 29, 1996; Limiting Oxygen Index (LOI), ASTM D-2863; and Cone Calorimetry, ASTM E-1354.

The effective amount of hindered amine needed to achieve flame retardancy is from 0.05 to 10% by weight based on the polymeric substrate; preferably 0.5 to 8% by weight; and most preferably 0.5 to 2% by weight.

The effective flame retarding amount of the synergistic mixture (b) containing components (i) and (ii) is 0.5 to 30% by weight based on component (a).

In that synergistic mixture (b), the effective flame retarding amount of a hindered amine is 0.5 to 10% by weight based on component (a); and preferably is 0.5 to 8% by weight based on component (a).

More particularly, the flame retardant compounds useful in the instant invention are preferably selected from the group consisting of polybrominated diphenyl oxide (DE-60F, Great Lakes Corp.)
decabromodiphenyl oxide (DBDPO; SAYTEX® 102E)
bis(2,3-dibromopropyl ether) of bisphenol A (PE68),
ammonium polyphosphate (APP) or (HOSTAFLAM® AP750),
brominated epoxy resin,
ethylene-bis(tetrabromophthalimide) (BT93),
1,2-bis(tribromophenoxy)ethane (FF680), and
tetrabmmo-bisphenol A (SAYTEXW RB® 100).

The following examples are meant for illustrative purposes only and are not to be construed to limit the scope of this invention in any manner whatsoever.

Coadditives found useful for use with the instant NOR-hindered amine compounds in flame retardant compositions are as follows:

Phosphorus Compounds:
tris(2,4-di-tert-butylphenyl) phosphite, (IRGAFOS® 168, Ciba Specialty Chemicals Corp.);
bis(2,4-di-tert-butyl-6-methylphenyl) ethyl phosphite, (IRGAFOS® 38, Ciba Specialty Chemicals Corp.);
2,2',2"-nitrilo[triethyl-tris-(3,3',5,5'-tetra-tert-butyl-1,1'-biphenyl-2,2'-diyl) phosphite], (IRGAFOS® 12, Ciba Specialty Chemicals Corp.);
tetrakis(2,4-di-butylphenyl) 4,4'-biphenylenediphosphonite, (IRGAFOS® P-EPQ, Ciba Specialty Chemicals Corp.);
tris(nonylphenyl) phosphite, (TNPP®, General Electric);
bis(2,4di-tert-butylphenyl) pentaerythrityl diphosphite, (ULTRANOX® 626, General Electric);
2,2'-ethylidenebis(2,4-di-tert-butylphenyl) fluorophosphite, (ETHANOX® 398, Ethyl Corp.)
2-butyl-2-ethylpropan-1,3-diyl 2,4,6-tri-tert-butylphenyl phosphite. (ULTRANOX® 641, General Electric).

Flame Retardants:
tris[3-bromo-2,2-bis(bromomethyl)propyl] phosphate, (PB 370®, FMC Corp.)
decabromodiphenyl oxide, (DBDPO);
ethylene bis-(tetrabromophthalimide), (SAYTEX® BT-93);
ethylene bis-(dibromo-norbomanedicarboximide), (SAYTEX® BN451)

UV Absorbers:
2-(2-hydroxy-3,5-di-α-cumylphenyl)-2H-benzotriazole, (TINUVIN® 234, Ciba Specialty Chemicals Corp.);
2-(2-hydroxy-5-methylphenyl)-2H-benzotriazole, (TINUVINO® P, Ciba Specialty Chemicals Corp.);
5-chloro-2-(2-hydroxy-3, 5di-tert-butylphenyl)-2H-benzotriazole, (TINUVIN® 327, Ciba Specialty Chemicals Corp.);
2-(2-hydroxy-3,5-di-tert-amylphenyl)-2H-benzotriazole, (TINUVIN® 328, Ciba Specialty Chemicals Corp.);

2-(2-hydroxy-3-β-cumyl-5-tert-octylphenyl)-2H-benzotriazole, (TINUVIN® 928, Ciba Specialty Chemicals Corp.);

2,4-di-tert-butylphenyl 3,5-di-tert-butyl-hydroxybenzoate, (TINUVIN® 120, Ciba Specialty Chemicals Corp.);

2-hydroxy4-n-octyloxybenzophenone, (CHIMASSORB® 81, Ciba Specialty Chemicals Corp.);

2,4-bis(2,4dimethyphenyl)-6-(2-hydroxy-4-octyloxyphenyl)-s-triazine, (CYASORB® 1164, Cytec).

TEST METHODS

NFPA 701 Standard Methods of Fire Tests for Flame-Resistant Textiles and Films, 1989 and 1996 editions;

UL 94 Test for Flammability of Plastic Materials for Parts in Devices and Appliances, 5th Edition, Oct. 29, 1996;

Limiting Oxygen Index (LOI), ASTM D-2863;

Cone Calorimetry, ASTM E-1 or ASTM E 1354;

ASTM D 2633-82, bum test.

TEST COMPOUNDS

NOR-1 is the mixture of compounds of formula I, II, IIA and III where R is cyclohexyl.

NOR-3 is bis(1-octyloxy-2,2,6,6-tetramethylpiperidin-4-yl) sebacate, (TINUVIN® 123, Ciba Specialty Chemicals Corp.).

NOR-9 is 1-(2-hydroxy-2-methylpropoxy)-4-octadecanoyloxy-2,2,6,6-tetramethylpiperidine.

NOR-10 is the compound of formula:

FR-4 is ammonium polyphosphatelsynergist blend, HOSTAFLAM® AP750.

FR-5 is decabmomodiphenyl oxide, SAYTEX® 102E.

FR-7 is melamine phosphate, MELAPUR® P 46.

FR-8 is ammonium polyphosphate, EXOLIT® AP752.

EXAMPLE 1

Fiber grade polypropylene, containing 0.05% by weight of calcium stearate and 0.05% of tris(2,4-di-tert-butylphenyl) phosphite and 0.05% of a N,N-dihydroxylamine made by the direct oxidation of N,N-di (hydrogenated tallow)amine is dry blended with the test additives and then melt compounded at 234° C. (450° F.) into pellets. The pelletized fully formulated resin is then spun at 246° C. (475° F.) into fiber using a Hills laboratory model fiber extruder. The spun tow of 41 filaments is stretched at a ratio of 1:3.2 to give a final denier of 615/41.

Socks are knitted from the stabilized polypropylene fiber on a Lawson-Hemphill Analysis Knitter and tested under NFPA 701 vertical bum procedure. The time in seconds for the knitted sock to extinguish after the insult flame is removed is reported as "After Flame". Both the maximum time for any one replicate and the total time for all ten replicates are shown in the table below. Efficacy as a flame retardant is demonstrated when low After Flame times are observed relative to a blank sample containing no flame retardant.

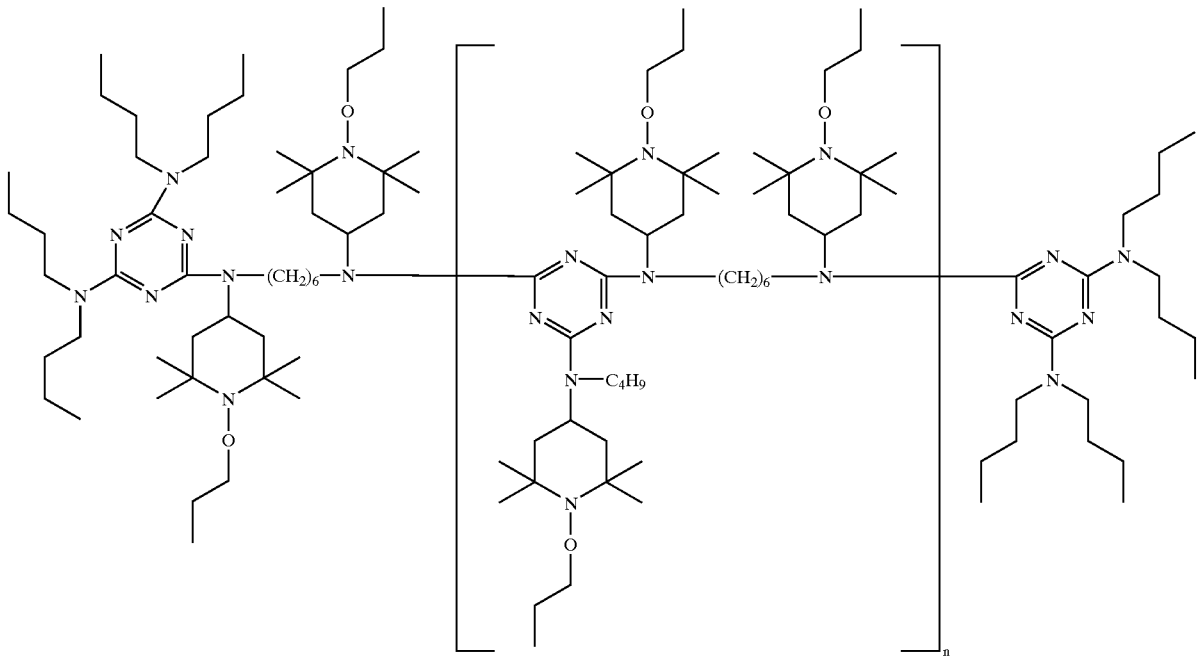

| (weight %) Formulation | Weight Loss % | Time sec | Drip Burn Pass/Fail |
|---|---|---|---|
| Control | 36 | >50 | Fail |
| FR-5 (4%) | 7 | 0.8 | Pass |
| FR-5 (2%) | 10 | 5 | Fail |
| FR-5 (1%) + NOR-1 (0.5%) | 4 | 0 | Pass |
| FR-5 (1%) + NOR-3 (0.5%) | 9 | 0.5 | Pass |
| FR-5 (1%) + NOR-9 (0.5%) | 5 | 0 | Pass |
| FR-5 (1%) + NOR-10 (0.5%) | 0.1 | 8 | Pass |

In the NFPA 701 test, a vertical piece of fabric is ignited with a Meeker burner. The flame is held on the fabric for 45 seconds. The drip burn time and the fabric weight loss are measured after the burning. To pass the NFPA 701 test, a material shoud loose less than 40% of weight and have a drip burn time of less than 2 seconds.

FR-5 at the 2% level fails the NFPA 701 test, but even at half that concentration in the presence of the instant hindered amines the flame retardancy performance is vastly improved.

It is clear that when some of the decabromodiphenyl oxide is replaced with a selected hindered amine that flame retardancy is actually enhanced even at a lower total concentration (2% versus 1.5%) enough to pass the NFPA 701 test.

The combination of decabromodiphenyl oxide and the selected hindered amine is synergistic. This result is both surprising and unexpected as well as allowing a lesser amount of a brominated compound to be used and still obtain adequate flame retardancy.

EXAMPLE 2

Polypropylene, the base resin containing 0.05% by weight of calcium stearate, 0.1% by weight of tris(2,4-di-tert-butylphenyl) phosphite and 0.05% by weight of neopentanetetrayl tetrakis(3,5-di-tert-butyl-4-hydroxyhydrocinnamate), is melt compounded on a single-screw extruder at 425° F. (218° C.) with the respective additives to form the formulations given in the table below. 125 mil plaques are compression molded at 400° F. (204° C.).

The plaques are tested for flame retardancy by the UL 94V thick section test.

| Formulation | 1st Flame Time (average seconds) | 2nd Flame Time (average seconds) |
|---|---|---|
| FR-4 (5%) | 252 | ** |
| FR-4 (10%) | 103 | ** |
| FR-4 (5%) + NOR-1 (5%) | 3 | 83 |
| FR-4 (10%) + NOR-1 (5%) | 5 | 4 |
| FR-4 (25%) | 7 | 11 |

**no time is shown for the 2nd flame since the sample is completely consumed after application of the first flame.

It is dear that the combination of the hindered amine NOR-1 with inorganic flame retardant at the same total concentration potentiates the effectiveness of the inorganic flame retardant allowing for a lower concentration of said inorganic flame retardant to be used when combined with the hindered amine component. This is a synergistic effect. Even when the inorganic flame retardant is used at very high levels alone, it cannot provide as much flame retardancy as the combination of said flame retardant with the hindered amine at a much lower total concentration.

EXAMPLE 3

Following the procedure of Example 2, molding grade polypropylene is dry blended with the test additives and then melt compounded at 425° F. (218° C.). Plaques (125 mil) are prepared by injection molding from the formulations using a Boy Injection Molder at 475° F. (246° C.). The specimens are tested for flame retardancy according to the UL-94 vertical burn test specifications: The results are shown below.

| (weight %) Formulation | First Flame Time (av seconds) | Second Flame Time (av seconds) |
|---|---|---|
| control | 194 | ** |
| FR-5 (10.5%) | 97 | 55 |
| FR-5 (10.5%) + Sb$_2$O$_3$ (3.5%) | 27 | 3 |
| FR-5 (5%) + NOR-1 (0.25%) | 22 | 11 |
| FR-5 (5%) + NOR-9 (0.25%) | 12 | 8 |
| FR-5 (5%) + NOR-10 (0.25%) | 8 | 18 |

**no time is shown for the 2nd flame since the sample is completely consumed after application of the first flame.

FR-5 at the 10.5% level does not provide adequate flame retardancy. However, when only half as much FR4 (5% level) is combined with a very small amount of an instant hindered amines (0.25%), the flame retardancy is greatly improved.

These data show that antimony oxide can be replaced with a small amount of an instant hindered amine in order to achieve good flame retardancy. This is important since the replacement of heavy metals is of prime concern for safety and environmental reasons.

EXAMPLE 4

Polyethylene fibers are prepared from fiber grade polyethylene by dry blending with test additives and melt compounding at 400° F. Fibers are extruded from this formulation using a Hills laboratory scale fiber extruder. Socks are knitted from the fibers and are tested for flame retardancy according to NFPA 701 vertical burn method. Polyethylene fibers contain an instant hindered amine compound in combination with a classic brominated flame retardant decabromodiphenyl oxide (DBDPO); bis(2,3dibromopropyl) ether of tetrabromobis phenol A (PE68); or ethylene bis-tetrabromophthalimide (SAYTEX® BT-93). These formulated fibers are tested for flame retardancy according to NFPA 701.

The fibers containing both an instant hindered amine compound and a classic brominated flame retardant exhibit enhanced flame retardancy compared to the classic flame retardant alone.

EXAMPLE 5

Polyethylene (LDPE) is melt compounded on a twin screw extruder at 450° F. (232° C.) with the respective additives to form the formulations given in the table below. 125 mil plaques are compression molded at 400° F. (204° C.).

The plaques are tested for flame retardancy by the UL 94V thick section test.

| Formulation | 1st Flame Time (average seconds) | 2nd Flame Time (average seconds) |
|---|---|---|
| Blank | 163 | |
| FR-4 (10%) | 198 | ** |
| FR-4 (5%) + NOR-1 (5%) | 118 | — |
| FR-4 (10%) + NOR-1 (5%) | 1 | 64 |

**no time is shown for the 2nd flame since the sample is completely consumed after the application of the first flame.

It is clear that the combination of the hindered amine NOR-1 with inorganic flame retardant at the same total concentration potentiates the effectiveness of the inorganic flame retardant allowing for a lower concentration of said inorganic flame retardant to be used when combined with the hindered amine component This is a synergistic effect

EXAMPLE 6

Foam grade polyethylene is dry blended with test additives and then melt compounded into pellets. The pelletized fully formulated resin is then blown into foam.

The polyethylene foam prepared contains an instant NOR or NOROL compound in combination with a classic brominated flame retardant. The formulated foam is tested for flame retardancy according to the UL-94 bum test method.

The foam containing both an NOR or NOROL compound and a classic brominated flame retardant exhibits enhanced flame retardancy compared to foam containing the classic halogenated flame retardant alone.

EXAMPLE 7

Wire & cable grade polyethylene is dry blended with test additives and then melt compounded into pellets. The pelletized fully formulated resin is then extruded onto wire.

Test specimens are tested for flame retardancy using the ASTM D 2633-82 bum test conditions. The formulations containing both an NOR or NOROL compound and a classic brominated flame retardant exhibits enhanced flame retardancy compared to the classic halogenated flame retardant alone.

EXAMPLE 8

Fiber grade polyethylene is dry-blended with test additives. In addition to a hindered amine, selected flame retardants are also included in the various formulations. Non-woven fabrics are produced from the polymer blend formulations by a spun-bonded or melt-blown process.

The non-woven fabrics made thereby are tested for flame retardancy according to the NFPA 701 vertical bum test specifications. The fabrics containing the hindered amine compounds and selected flame retardants exhibit flame retardancy.

EXAMPLE 9

Fiber grade polypropylene is dry-blended with test additives. In addition to a hindered amine, selected brominated flame retardants are also included in the various formulations. Non-woven fabrics are produced from the polymer blend formulations by a spun-bonded or melt-blown process.

The non-woven fabrics made thereby are tested for flame retardancy according to the NFPA 701 vertical bum test specifications. The fabrics containing the hindered amine compounds and selected brominated flame retardants exhibit flame retardancy.

EXAMPLE 10

Molding grade polystyrene is dry-blended with test additives and then melt compounded. In addition to the hindered amines, selected brominated flame retardants are also included in the test formulations. Specimens are injection molded from these test formulations.

The specimens are tested for flame retardancy according to the UL-94 bum test specifications. The molded specimens containing the hindered amine compounds and selected brominated flame retardants exhibit flame retardancy.

EXAMPLE 11

Foam grade polystyrene is dry-blended with test additives and then melt compounded. In addition to the hindered amines, selected brominated flame retardants are also included in these test formulations. Foam polystyrene specimens are prepared from these test formulations.

The specimens are tested for flame retardancy according to the UL-94 bum test specifications. The foam specimens containing the hindered amine compounds and brominated flame retardants exhibit flame retardancy.

EXAMPLE 12

Molding grade ABS is dry blended with the test additives and then melt compounded at 425° F. (218° C.). Specimens 125 mil (⅛") thick are then injection molded from this formulation using a Boy Injection Molder at 450° F. (232° C.). The specimens are tested for flame retardancy according to the UL-94 vertical bum test specifications. The results are tabulated below.

| (weight %) Formulation | 1st Flame Time (average seconds) | 2nd Flame Time (average seconds) |
|---|---|---|
| control | 141 | ** |
| FR-5 (5%) | 68 | 18 |
| FR-5 (10%) | 42 | 28 |
| FR-5 (7.5%) + NOR-1 (0.25%) | 30 | 13 |
| FR-5 (5%) + NOR-1 (0.25%) | 39 | 20 |

**no time is shown for the 2nd flame since the sample is completely consumed after application of the first flame.

It is clear that the combination of the hindered amine NOR-1 with an organic flame retardant at essentially the same total concentration potentates the effectiveness of the organic flame retardant allowing for a lower concentration of said organic flame retardant to be used when combined with the hindered amine component. This is a synergistic effect.

Even when the organic flame retardant is used at very high levels alone, it cannot provide as much flame retardancy as the combination of said flame retardant with the hindered amine at a much lower total concentration.

EXAMPLE 13

Following the general procedure of Example 2, molding grade polypropylene is dry blended with the test additives and then melt compounded at 425° F. (218° C.). Specimens 125 mil (⅛") thick are then injection molded from this formulation at 450° F. (232° C.). The specimens are tested for flame retardancy according to the UL-94 horizontal burn test specifications. The results are tabulated below.

| (weight %) Formulation | Burn Time (seconds) | | | |
|---|---|---|---|---|
| | Specimen 1 | Specimen 2 | Specimen 3 | Total |
| FR-7 (5%) | 186 | 182 | 180 | 548 |
| FR-7 (5%) + NOR-1 (0.5%) | 3 | 35 | 25 | 63 |
| FR-7 (2.5%) + NOR-1 (1%) | 132 | 13 | 24 | 169 |
| FR-7 (2.5%) + NOR-10 (1%) | 2 | 1 | 1 | 4 |
| FR-8 (10%) | 282 | 271 | 172 | 725 |
| FR-8 (5%) + NOR-1 (1%) | 3 | 8 | 5 | 16 |
| FR-8 (5%) + NOR-10 (1%) | 2 | 1 | 2 | 5 |

It is clear that the combination of the hindered amine NOR-1 or NOR-10 with an inorganic or organic flame retardant at essentially the same and even at a lesser total concentration potentiates the effectiveness of the inorganic or organic flame retardant allowing for a lower concentration of said inorganic or organic flame retardant to be used when combined with the hindered amine component. This is a synergistic effect.

Even when the inorganic or organic flame retardant is used at very high levels alone, it cannot provide as much flame retardancy as the combination of said flame retardant with the hindered amine at a much lower total concentration.

What is claimed is:

1. A flame retardant polymer composition which comprises
(a) a polymer substrate, and
(b) an effective flame retarding amount of a synergistic mixture of
  (i) a hindered amine and
  (ii) a brominated and/or phosphorus containing flame retardant;
  wherein the hindered amine of component (i) is selected from the group consisting of (A) and (B), wherein
  (A) is:

$$\left[ \begin{array}{c} RCH_2 \diagup CH_3 \diagdown R \\ E-N \phantom{xxx} O-R_2 \\ RCH_2 \diagdown CH_3 \diagup \end{array} \right]_m \quad (A)$$

wherein
E is cyclohexyloxy,
R is hydrogen or methyl,
m is 1 to 4,
when m is 1,
$R_2$ is hydrogen, $C_1$–$C_{18}$alkyl or said alkyl optionally interrupted by one or more oxygen atoms, $C_2$–$C_{12}$alkenyl, $C_6$–$C_{10}$aryl, $C_7$–$C_{18}$aralkyl, glycidyl, a monovalent acyl radical of an aliphatic, cycloaliphatic or aromatic carboxylic acid, or a carbamic acid, or:

[chemical structure with C(CH₃)₃ groups, HO-, and repeat unit x]

wherein x is 0 or 1, or:

[piperidine-based chemical structure with CH₃ groups, (CH₂)ᵧN, and CH₂-C(O)]

wherein y is 2–4;
when m is 2,
$R_2$ is $C_1$–$C_{12}$alkylene, $C_4$–$C_{12}$alkenylene, xylylene, a divalent acyl radical of an aliphatic, cycloaliphatic, araliphatic or aromatic dicarboxylic acid or of a dicarbamic acid, or:

[structures with $D_1$, $D_2$, $D_3$ and C=O groups]

$$-\overset{O}{\underset{\|}{C}}-NH-(CH_2)_d-NH-\overset{O}{\underset{\|}{C}}-$$

wherein $D_1$ and $D_2$ are independently hydrogen, an alkyl radical containing up to 8 carbon atoms, an aryl or aralkyl radical including 3,5-di-t-butyl4-hydroxybenzyl radical, $D_3$ is hydrogen, or an alkyl or alkenyl radical containing up to 18 carbon atoms, and d is 0–20;
when m is 3, $R_2$ is a trivalent acyl radical of an aliphatic, unsaturated aliphatic, cycloaliphatic, or aromatic tricarboxylic acid;
when m is 4, $R_2$ is a tetravalent acyl radical of a saturated or unsaturated aliphatic or aromatic tetracarboxylic acid including 1,2,3,4-butanetetracarboxylic acid, 1,2,3,4-but-2-enetetracarboxylic acid, and 1,2,3,5- and 1,2,4,5-pentanetetracarboxylic acid;
wherein
(B) is a mixture of N,N',N'''-tris{2,4-bis[(1-hydrocarbyloxy-2,2,6,6-tetramethylpiperidin--4-yl)alkyl-amino]-s-triazin-6-yl}-3,3'-ethylenediiminodipropylamine; N,N',N''-tris{2,4-bis[(1-hydrocarbyloxy-(2,2,6,6-tetramethylpiperidin-4-yl)alkylamino]-s-triazin-6-yl}-3,3'-ethylenediiminodipropylamine, and bridged derivatives as described by formulas I, II, IIA and III:

$R_1NH—CH_2CH_2CH_2NR_2CH_2CH_2NR_3CH_2CH_2CH_2NHR_4$ (I)

$T—E_1—T_1$ (II)

$T—E_1$ (IIA)

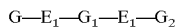 (III)

where in the tetraamine of formula I:
  $R_1$ and $R_2$ are the s-triazine moiety E; and one of $R_3$ and $R_4$ is the s-triazine moiety E with the other of $R_3$ or $R_4$ being hydrogen,
  E is:

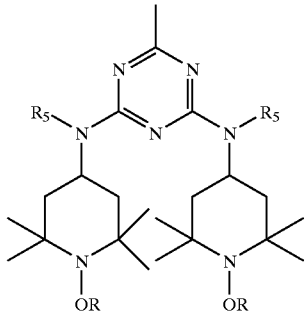

R is cyclohexyl,
$R_5$ is alkyl of 1 to 12 carbon atoms, where in the compound of formula II or IIA when R is cyclohexyl,
T and $T_1$ are each substituted by $R_1$–$R_4$ as is defined for formula I, where
  (1) one of the s-triazine moieties E in each tetraamine is replaced by the group $E_1$ which forms a bridge between two tetraamines T and $T_1$,
$E_1$ is:

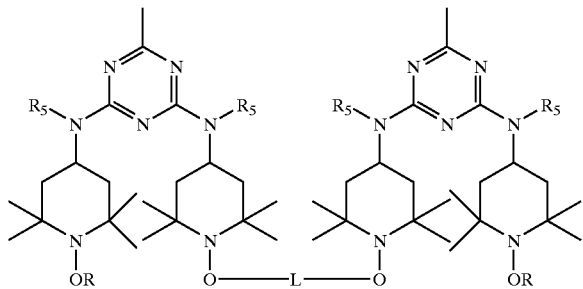

or
  (2) the group $E_1$ can have both termini the same tetraamine T as in formula IIA where two of the E moieties of the tetraamine are replaced by one $E_1$ group, or
  (3) all three s-triazine substituents of tetraamine T can be $E_1$ such that one $E_1$ links T and $T_1$ and a second $E_1$ has both termini in tetraamine T,
L is cyclohexanediyl;
where in the compound of formula III:
  G, $G_1$ and $G_2$ are each tetraamines substituted by $R_1$–$R_4$ as defined for formula I, except that G and $G_2$ each have one of the s-triazine moieties E replaced by $E_1$, and $G_1$ has two of the triazine moieties E replaced by $E_1$, so that there is a bridge between G and $G_1$ and a second bridge between $G_1$ and $G_2$;
  which mixture is prepared by reacting two to four equivalents of 2,4-bis[(1-hydrocarbyloxy-2,2, 6,6-piperidin-4-yl)butylamino]-6-chloro-triazine with one equivalent of N,N'-bis(3-aminopropyl)-ethylenediamine; and with the proviso that when the polymer substrate is polypropylene, the flame retardant is not a halogenated hydrocarbyl phosphate or phosphonate; and with the proviso that when the polymer substrate is polypropylene, the flame retardant is not a brominated flame retardant when component (i) is di-(1-cyclohexyloxy-2,2,6,6-tetramethylpiperidin-4-yl) sebacate or di-(1-cyclohexyloxy-2,2,6,6-tetramethylpiperidin4-yl) succinate.

2. A composition according to claim 1 wherein the polymer substrate is selected from the group of resins consisting of the polyolefins, the thermoplastic olefins, styrenic polymers and copolymers, and ABS.

3. A composition according to claim 2 wherein the polymer substrate is polypropylene, polyethylene, thermoplastic olefin (TPO), ABS and high impact polystyrene.

4. A composition according to claim 3 wherein the polymer substrate is polypropylene, polyethylene or thermoplastic olefin (TPO).

5. A composition according to claim 1 wherein the effective flame retarding amount of a hindered amine of component (i) is 0.05 to 10% by weight based on the polymer substrate.

6. A composition according to claim 5 wherein the effective flame retarding amount of a hindered amine of component (i) is 0.5 to 8% by weight based on the polymer substrate.

7. A composition according to claim 6 wherein the effective flame retarding amount of a hindered amine of component (i) is 0.5 to 2% by weight based on the polymer substrate.

8. A composition according to claim 1 wherein the effective flame retarding amount of the synergistic mixture of component (b) is 0.5 to 30% by weight based on component (a).

9. A composition according to claim 1 wherein the flame retardant component (ii) is selected from the group consisting of:
  polybrominated diphenyl oxide (DE60F)
  decabromodiphenyl oxide (DBDOP),
  bis(2,3-dibromopropyl ether) of bisphenol A (PE68),
  ammonium polyphosphate (APP) or (HOSTAFLAM® AP750),
  resorcinol diphosphate oligomer (RDP),
  brominated epoxy resin,
  ethylene-bis(tetrabromophthalimide) (BT93),
  1,2-bis(tribromophenoxy)ethane (FF680), and
  tetrabromo-bisphenol A (SAYTEX® RB100).

10. A composition according to claim 9 wherein the flame retardant compound (ii) is ammonium polyphosphate or decabromodiphenyl oxide.

11. A composition according to claim 1 wherein the coadditive is a phosphorus compound selected from the group consisting of tris(2,4-di-tert-butylphenyl) phosphite, bis(2,4di-tert-butyl-6-methylphenyl) ethyl phosphite, 2,2', 2"-nitrilo[triethyl-tris-(3,3',5,5'-tetra-tert-butyl-1,1'-biphenyl-2,2'-diyl) phosphite], tetrakis(2,4di-butylphenyl) 4,4'-biphenyiene-diphosphonite, tris(nonylphenyl) phosphite, bis(2,4di-tert-butylphenyl) pentaerythrityl diphosphite, 2,2'-ethylidenebis(2,4di-tert-butylphenyl) fluorophosphite and 2-butyl-2-ethyl-propan-1,3-diyl 2,4,6-tri-tert-butylphenyl phosphite; or a UV absorber selecte from the group consisfing of 2-(2-hydroxy-3,5-di-α-acumylphenyl)-2H-benzotriazole, 2-(2-hydroxy-5methyl-phenyl)-2H-benzotriazole, 5-chloro-2-(2-hydroxy-3,5-di-tert-butylphenyl)-2H-benzotriazole, 2-(2-hydroxy-3,5-ditert-amylphenyl)-2H-benzotriazole, 2-(2-hydroxy-3-α-acumyl-5-tert-octyl-phenyl)-2H-benzotriazole, 2,4-di-tert-butylphenyl 3,5-di-tert-butyi4hydroxybenzoate, 2-hydroxy-4-n-octyloxybenzophenone and 2,4-bis(2,4dimethyphenyl)-6-(2-hydroxy-4 octyloxy-phenyl)-s-triazine.

12. A composition according to claim 1 wherein the hindered amine of component (i) is (a) the mixture of compounds of formula I, II, IIA and III where R is cyclohexyl;

(b) 1-cyclohexyloxy-2,2,6,6-tetramethyl-4-octadecylaminopiperidine;

(d) 2,4-bis[(1-cyclohexyloxy-2,2,6,64etramethylpiperidin-4-yl)butylamino]-6-(2-hydroxyethyl-amino-s-triazine;

(e) bis(1-cyclohexyloxy-2,2,6,6-tetramethylpiperidin-4-yl) adipate;

(g) the oligomeric compound which is the condensation product of 4,4'-hexamethylene-bis(amino-2,2,6,6-tetramethylpiperidine) and 2,4-dichloro-6-[(1-cyclohexyloxy-2,2,6,6-tetramethyl-piperidin-4-yl)butylamino]-s-triazine end-capped with 2-chloro4,6-bis(dibutylamino)-s-triazine; or (h) 2,4-bis[(1-cyclohexyloxy-2,2,6,6-piperidin-4-yl)butylamino]-6-chloro-s-triazine.

* * * * *